(12) United States Patent
Schäfter

(10) Patent No.: US 7,498,457 B2
(45) Date of Patent: Mar. 3, 2009

(54) PROCESS FOR PREPARING SOLID PARTICLES OF PHENOLIC ANTIOXIDANTS

(75) Inventor: Johannes Schäfter, Lörrach (DE)

(73) Assignee: Ciba Specialty Chemicals Corp., Tarrytown, NY (US)

( * ) Notice: Subject to any disclaimer, the term of this patent is extended or adjusted under 35 U.S.C. 154(b) by 0 days.

(21) Appl. No.: 11/632,684

(22) PCT Filed: Jul. 18, 2005

(86) PCT No.: PCT/EP2005/053425

§ 371 (c)(1),
(2), (4) Date: Jan. 17, 2007

(87) PCT Pub. No.: WO2006/010718

PCT Pub. Date: Feb. 2, 2006

(65) Prior Publication Data

US 2007/0244342 A1    Oct. 18, 2007

(30) Foreign Application Priority Data

Jul. 27, 2004    (EP) ................... 04103591

(51) Int. Cl.
*C07C 69/76*    (2006.01)
(52) U.S. Cl. .......................... 560/75; 560/75
(58) Field of Classification Search .................. 560/75
See application file for complete search history.

(56) References Cited

U.S. PATENT DOCUMENTS

| 3,644,482 A | 2/1972 | Dexter et al. ............... 260/473 |
| 4,547,585 A | 10/1985 | Yamanaka et al. ............ 560/75 |
| 4,683,326 A | 7/1987 | Orban et al. .................. 560/75 |
| 7,262,319 B2 * | 8/2007 | Rehm et al. ................... 560/75 |

FOREIGN PATENT DOCUMENTS

| EP | 0026893 | 4/1981 |
| EP | 0403431 | 12/1990 |
| EP | 403431 A2 * | 12/1990 |
| EP | 0448775 | 10/1991 |
| EP | 448775 A2 * | 10/1991 |
| WO | 99/33555 | 7/1999 |
| WO | 03/081690 | 10/2003 |
| WO | 2004/048312 | 6/2004 |

OTHER PUBLICATIONS

English language abstract for EP 0026893, Apr. 15, 1981.

* cited by examiner

*Primary Examiner*—Daniel M Sullivan
*Assistant Examiner*—Sudhakar Katakam
(74) *Attorney, Agent, or Firm*—Tyler A. Stevenson

(57) ABSTRACT

The invention relates to a process for preparing solid particles comprising a phenolic antioxidant in essentially crystalline form and to the process step of further processing the phenolic antioxidants. Solid particles are prepared from a melt of the phenolic antioxidants are added to a dispersion comprising the solid particles of the compound (I) in a mixture of an organic water-miscible solvent and water and the crystals obtained from the dispersion are separated.

9 Claims, No Drawings

PROCESS FOR PREPARING SOLID PARTICLES OF PHENOLIC ANTIOXIDANTS

The invention relates to a process for preparing solid particles comprising a phenolic antioxidant in essentially crystalline form and to the process step of further processing the phenolic antioxidants.

Solid phenolic additives, such as commercial antioxidants from the Irganox® and Irgafos® (trade marks of Ciba Specialty Chemicals) series, e.g. IRGANOX 1010: pentaerythritol tetrakis[3-(3,5-di-tert-butyl4-hydroxyphenyl)-propionate], IRGANOX 1098: N,N'-hexane-1,6-diyl-bis[3-(3,5-di-tert-butyl-4-hydroxyphenylpropionamide)], or IRGAFOS 168: tris(2,4-di-t-butylphenyl)phosphite, are used for a great variety of technical applications, e.g. for the stabilisation of polymers against oxidative, thermal or light induced degradation.

These additives are commercially available in the form of solid particles, e.g. powders, comminuted powders or granulate. The preparation of these particles from liquid reaction mixtures requires a separation step from the liquid phase.

The separation of solid particles obtained in crystal form from liquid reaction mixtures has certain drawbacks. The formation of crystalline particles in a liquid phase is a time consuming process that has to be carefully monitored with regard to the composition of the liquid phase, concentration and temperature.

The preparation of solid phenolic antioxidants, such as IRGANOX 1010 or 1098, from a melt phase, as opposed to a crystallisation process, has certain drawbacks, too. Large amounts of amorphous particles are formed from the melt phase. It has been found that amorphous particles of these phenolic antioxidants are subject to undesirable discolouration processes. An explanation for this effect is the possible migration of oxygen in amorphous material. The crystal lattice of crystalline material would prevent the migration of oxygen.

Therefore, solid phenolic antioxidants, such as IRGANOX 1010 or 1098, are presently isolated in crystal form from the solvent methanol, which reduces the formation of amorphous material. The further processing of particles obtained from solution, such as crystals, to dry particle forms, such as granulates, bears the risk of undesirable dust formation resulting from abrasion, attrition or inter-particle friction. The formation of dust is a well-known problem that may eventually extend as far as dust explosion. More common are feeding problems when producing precise and reproducible weight amounts. A possible explanation is given by the lack of homogeneity and irregular shape of the particles formed.

Therefore, the present invention relates to the problem of preparing solid particles of improved homogeneity of the phenolic antioxidants mentioned.

According to EP-A-0 403 431, solid particles of phenolic antioxidants, such as IRGANOX 1010, are prepared by introducing a melt of the phenolic antioxidant into a cold agitated solution of an organic water-miscible solvent, such as methanol, and isolating the particles obtained. The disadvantage of this process is seen in the fact that mixtures of solid particles of low homogeneity are obtained which contain varying amounts of amorphous and crystalline material.

According to WO 2004/048312 solid particles of phenolic antioxidants, such as IRGANOX 1010 or 1098, are obtained from an aqueous phase to which a selected non-ionic surfactant, e.g. Tween®80, and larger amounts of seed crystals have been added.

It is desirable to avoid the addition of the surfactant and large amounts of seed crystals and to improve the homogeneity of the particles obtained according to that method.

It has surprisingly been found that the formation of solid particles prepared from a melt of the above-mentioned phenolic antioxidants, e.g. IRGANOX 1010 or 1098 or IRGAFOS 168, and the addition of the solid particles to an aqueous dispersion of these phenolic antioxidants in an organic water-miscible solvent produces solid particles in essentially crystalline form.

Therefore, the present invention relates to a process for preparing solid particles comprising an essentially crystalline form of a compound of the formula:

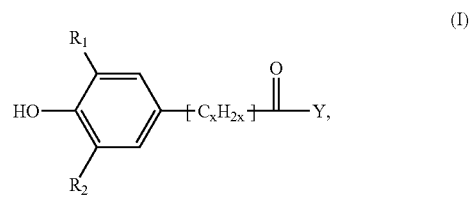
(I)

Wherein

One of $R_1$ and $R_2$ independently of one another represents hydrogen or $C_1$-$C_4$alkyl and the other one represents $C_3$-$C_4$alkyl;

x represents zero (direct bond) or a numeral from one to three; and

Y represents $C_8$-$C_{22}$alkoxy or groups of the partial formulae:

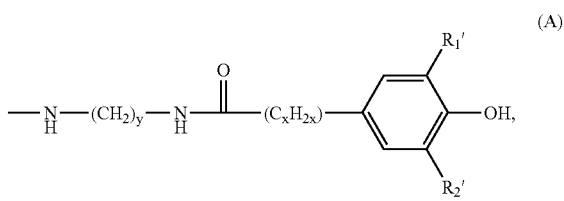
(A)

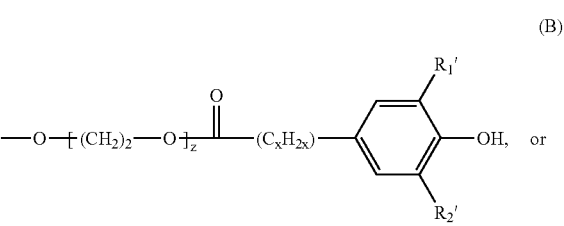
(B)

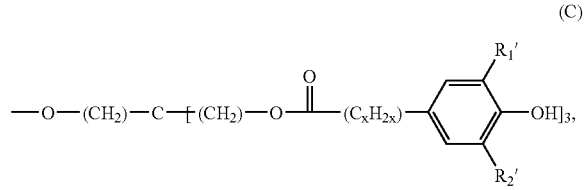
(C)

Wherein

One of $R_1'$ and $R_2'$ independently of one another represents hydrogen or $C_1$-$C_4$alkyl and the other one represents $C_3$-$C_4$alkyl;

x represents zero (direct bond) or a numeral from one to three;

y represents a numeral from two to ten; and z represents a numeral from two to six;

or a compound (II) selected from the group of organic phosphites and phosphonites, characterised in that solid particles are prepared from a melt of the compound (I), wherein $R_1$, $R_2$, $R_1'$, $R_2'$, Y, x, y and z are as defined above, or from a melt of the compound (II) or from mixtures thereof and added to a dispersion comprising the solid particles of the compound (I) or (II) or a mixture thereof in a mixture of an organic water-miscible solvent and water, and the crystals obtained from the dispersion are separated. Claim 1

The general terms used in the description of the instant invention, unless defined otherwise, are defined as follows:

The term solid particle form defines any aggregates or agglomerates of solid particulate matter, such as powders, crystals, comminuted crystals or granulates prepared from crystals and the like.

The term crystalline form defines any solid matter, wherein the molecules are arranged in a geometrically regular pattern, as opposed to amorphous forms.

The term in essentially crystalline form defines the exclusion of substantial amounts of amorphous particles from any compositions or agglomerates of crystalline particles. In a preferred embodiment of the invention less than 1% of amorphous partides are present in crystal isolates. In a particularly preferred embodiment of the invention less than 0.5% of amorphous particles are present in crystal isolates.

In a compound of the formula (I) $R_1$ and $R_2$ defined as $C_1$-$C_4$alkyl comprise the unbranched and branched (where possible) groups methyl, ethyl, n-propyl, isopropyl, n-butyl, isobutyl and tert-butyl.

$R_1$ and $R_2$ defined as $C_3$-$C_4$alkyl comprises unbranched and preferably branched groups, e.g. isopropyl, isobutyl or tert-butyl.

In a preferred embodiment of the invention one of $R_1$ and $R_2$ represents hydrogen or $C_1$-$C_4$alkyl, particularly methyl or tert-butyl, and the other one represents $C_3$-$C_4$alkyl, particularly tert-butyl.

In a compound (I) the index x represents zero (direct bond) or a numeral from one to three. In the event that x is zero, the direct bond is defined.

In the event that x is one, the group —$[C_xH_{2x}]$— represents methylene.

In a preferred embodiment x represents two. In that case the group —$[C_xH_{2x}]$— represents 1,1- or preferably 1,2-ethylene.

In the event that x represents the numeral three, the group —$[C_xH_{2x}]$— represents 1,1-, 1,2- or preferably 1,3-propylene.

Y defined as $C_8$-$C_{22}$alkoxy represents, for example, n-octyloxy, 2-ethylhexyloxy, 1,1,3,3-tetra-methylbutoxy, 1-methylheptyloxy, n-nonyloxy or 1,1,3-trimethylhexyloxy or $C_{10}$-$C_{22}$alkoxy, particularly straight chained $C_{10}$-$C_{22}$alkoxy, e.g. n-decyloxy, n-dodecyloxy n-tetradecyloxy, n-hexadecyloxy or n-octadecyloxy or higher homologues thereof.

In the groups of the partial formulae (A), (B) and (C) $R_1'$ and $R_2'$ defined as $C_1$-$C_4$alkyl are identical with $R_1$ and $R_2$ defined above.

In a group of the partial formula (A) x represents zero (direct bond) or a numeral from one to three and y represents a numeral from two to ten. In a preferred embodiment x represents two and y represents six.

In a group of the partial formula (B) x represents zero (direct bond) or a numeral from one to three and z represents a numeral from two to ten. In a preferred embodiment x represents two and z represents three.

In a group of the partial formula (C) x represents zero (direct bond) or a numeral from one to three and z represents a numeral from two to ten. In a preferred embodiment x represents two.

A particularly preferred compound (I), wherein Y represents a group of the partial formula (A), one of $R_1$ and $R_2$ and correspondingly one of $R_1'$ and $R_2'$ represents methyl and the other one represents tert-butyl, x represents two and y represents six, is IRGANOX 1098: N,N'-hexane-1,6-diyl-bis[3-(3,5-di-tert-butyl-4-hydroxyphenylpropionamide)].

A particularly preferred compound (I), wherein Y represents a group of the partial formula (B), one of $R_1$ and $R_2$ and correspondingly one of $R_1'$ and $R_2'$ represents methyl and the other one represents tert-butyl, x represents two and z represents two, is IRGANOX 245: ethylene bis(oxyethylene)-bis[3-(5-tert-butyl-4-hydroxy-m-tolyl)-propionate], CAS No. 36443-68-2.

A particularly preferred compound (I), wherein Y represents a group of the partial formula (C), $R_1$ and $R_2$ and correspondingly $R_1'$ and $R_2'$ represent tert-butyl and x represents two, is IRGANOX 1010: pentaerythritol tetrakis[3-(3,5-di-tert-butyl-4-hydroxy-phenyl)-propionate].

Compounds (II) selected from the group of organic phosphites and phosphonites are, in particular, triphenyl phosphite, diphenyl alkyl phosphite, phenyl dialkyl phosphites, tris(nonyl-phenyl) phosphite, trilauryl phosphite, trioctadecyl, phosphite, distearyl pentaerythritol di-phosphite, tris(2,4-di-tert-butylphenyl) phosphite (Irgafos® 168, Ciba Specialty Chemicals), diisodecyl pentaerythritol diphosphite, bis(2,4-di-tert-butylphenyl)pentaerythritol diphosphite (formula (d) below), bis(2,6-di-tert-butyl-4-methylphenyl) pentaerythritol diphosphite (formula (e)), bisisodecyloxypentaerythritol diphosphite, bis(2,4-di-tert-butyl-6-methylphenyl) pentaerythritol diphosphite, bis(2,4,6-tri-tert-butylphenyl)pentaerythritol diphosphite, tristearyl sorbitol triphosphite, tetrakis(2,4-di-tert-butylphenyl) 4,4'-biphenylenediphosphonite (Irgafos®PEP-Q, Ciba Specialty Chemicals, formula (h)), 6-isooctyloxy-2,4,8,10-tetra-tert-butyl-12H-dibenzo[d,g]-1,3,2-dioxaphosphocin (formula (c)), 6-fluoro-2,4,8,10-tetra-tert-butyl-12-methyldibenzo[d,g]-1,3,2-dioxaphosphocin (formula (a)), bis(2,4-di-tert-butyl-6-methylphenyl) methyl phosphite, bis(2,4-di-tert-butyl-6-methylphenyl)ethyl phosphite (formula (g)).

Particular preference is given to tris(2,4-di-tert-butylphenyl)phosphite, tris(nonylphenyl) phosphite and the following phosphites and phosphonites:

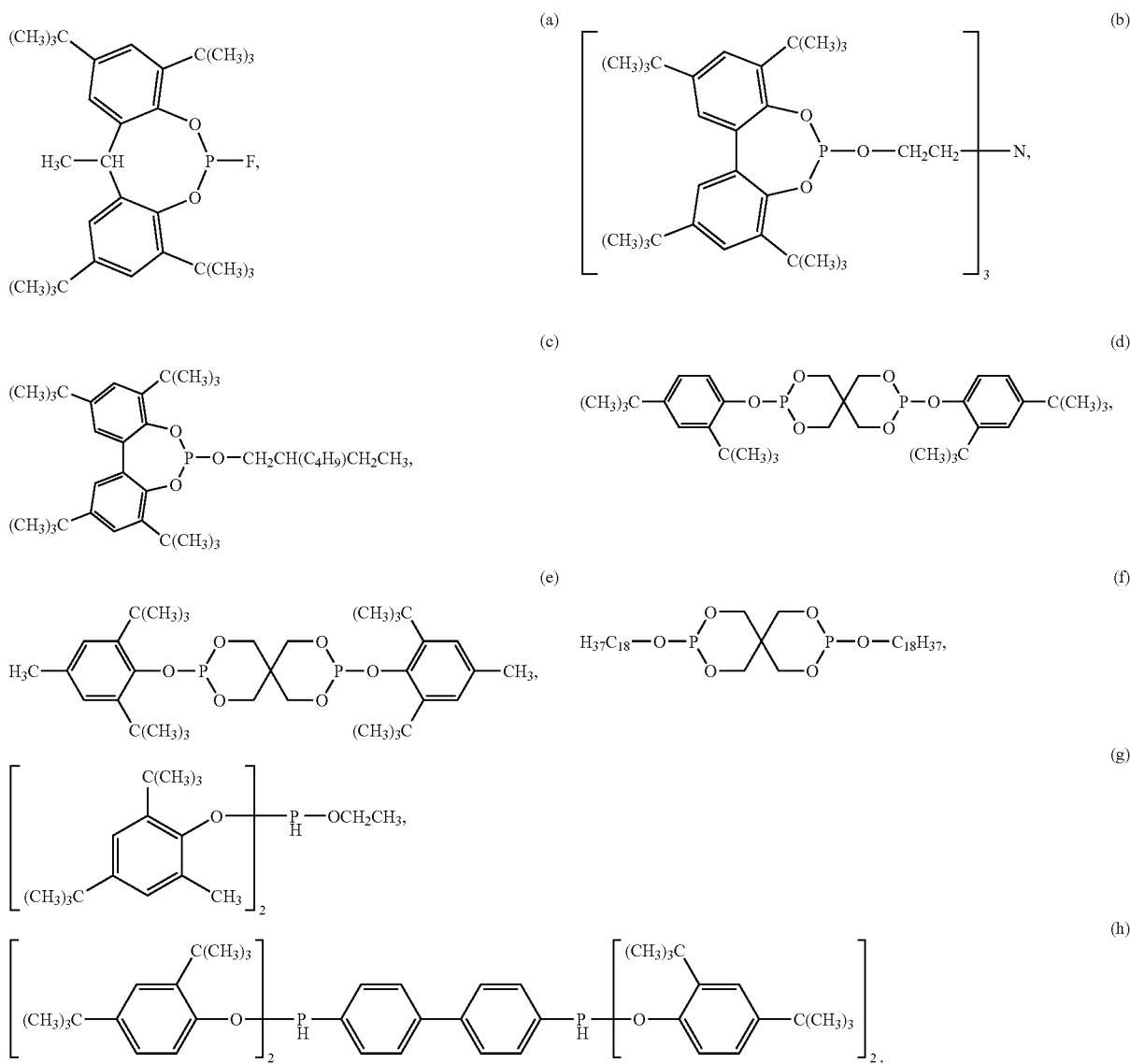

Very particular preference is given to tris(2,4-di-tert-butylphenyl)phosphite, bis(2,4-di-tert-butyl-6-methylphenyl) ethyl phosphite and tetrakis(2,4-di-tert-butylphenyl)-4,4'-biphenylenediphosphonite.

The abovementioned organic phosphites and phosphonites are known compounds; many of them are available commercially.

A preferred embodiment of the invention relates to a process for preparing solid particles comprising an essentially crystalline form of a compound (I), wherein One of $R_1$ and $R_2$ independently of one another represents hydrogen or $C_1$-$C_4$alkyl and the other one represents $C_3$-$C_4$alkyl;

x represents zero (direct bond) or a numeral from one to three; and

Y represents $C_8$-$C_{22}$alkoxy or groups of the partial formulae (A), (B) or (C), wherein One of $R_1'$ and $R_2'$ independently of one another represents hydrogen or $C_1$-$C_4$alkyl and the other one represents $C_3$-$C_4$alkyl;

x represents zero (direct bond) or a numeral from one to three;

y represents a numeral from two to ten; and z represents a numeral from two to six;

or of tris(2,4-di-tert-butylphenyl)phosphite (II), characterised in that solid particles are prepared from a melt of the compound (I), wherein $R_1$, $R_2$, $R_1'$, $R_2'$, Y, x, y and z are as defined above, or from a melt of the compound (II) or from mixtures thereof and added to a dispersion comprising the solid particles of the compound (I) or (II) or a mixture thereof in a mixture of an organic water-miscible solvent and water, and the crystals obtained from the dispersion are separated. Claim 3

A particularly preferred embodiment of the invention relates to a process for preparing solid particles comprising an essentially crystalline form of a compound (I) or a mixture thereof, wherein One of $R_1$ and $R_2$ independently of one another represents hydrogen or tert-butyl and the other one represents tert-butyl;

x represents two; and

Y represents $C_8$-$C_{22}$alkoxy; or groups of the partial formulae (A), (B) or (C), Wherein One of $R_1'$ and $R_2'$ independently of one another represents hydrogen or tert-butyl and the other one represents tert-butyl;

x represents two; y represents six; and z represents two, which is characterised in that the above-mentioned process steps are carried out. Claim 4

A highly preferred embodiment of the invention relates to a process for preparing solid particles comprising an essentially crystalline form of pentaerythritol tetrakis[3-(3,5-di-tert-butyl-4-hydroxyphenyl)-propionate] or N,N'-hexane-1,6-diyl-bis[3-(3,5-di-tert-butyl-4-hydroxy-phenylpropionamide)] or mixtures thereof. Claim 5

The term dispersion comprises any mixture of two phases wherein dispersed particles are distributed in a dispersant phase (dispergens), which in the instant case is a mixture of water and a water miscible solvent.

The dispersion is defined within the limits of so-called solid/liquid disperse systems, e.g. suspensions, as opposed to other types of dispersions, such as liquid/liquid, e.g. emulsions, solid/gas, e.g. fumes, or gas/liquid, e.g. foams, dispersions.

In the instant case, solid particles, e.g. granulates, seed crystals or amorphous particles of the compounds (I) or (II), are dispersed in the liquid phase, e.g. water or an aqueous alcoholic solution.

The term organic water-miscible solvent defines polar protic and aprotic solvents, such as $C_1$-$C_5$alkanols, e.g. methanol, ethanol, isopropanol, as well as acetone, acetonitrile, di-methylformamide or ethylene glycol.

In a preferred embodiment of the invention a $C_1$-$C_5$alkanol, e.g. methanol, is used.

A preferred embodiment of the invention relates to a process, which is characterised in that solid particles are prepared from a melt, which comprises the compound (I), wherein $R_1$, $R_2$, $R_1'$, $R_2'$, Y, x, y and z are as defined above, or a compound (II) selected from the group of organic phosphites and phosphonites or mixtures thereof and added to a dispersion comprising the solid particles of the compounds (I) or (II) or mixtures thereof in a mixture of a $C_1$-$C_5$alkanol and water. Claim 6

According to a particularly preferred embodiment of the invention solid particles are added to an aqueous mixture of methanol. Claim 7

According to another particularly preferred embodiment of the invention solid particles are added to an aqueous mixture of a $C_1$-$C_5$alkanol, e.g. methanol, and water at temperatures between 0°-50° C., preferably at temperatures between 20°-30° C. Claim 9

The solid particles are prepared by heating a compound (I) or (II) or a mixture thereof to temperatures, preferably between 80° C. and 200° C., to give a melt which is disintegrated into fine particles by known methods, such as pastillation (Sandvik), jet disintegration in gas or liquid, forced jet integration in gas or liquid, rotoforming techniques, extrusion and the like. The fine particles are subsequently fully or at least partially solidified by known methods, e.g. in a cooling belt, fluidised bed, in a pipe fall tower in the presence of a co-current or counter current cooling gas, e.g. liquid nitrogen or vapor from solidified $CO_2$. The solidification may be complete or partially complete thus generating fine particles with a soft or even liquid core and a solidified shell.

A preferred embodiment relates to a process, wherein solid particles are prepared from a melt, which comprises the compound (I), wherein $R_1$, $R_2$, $R_1'$, $R_2'$, Y, x, y and z are as defined above, or a mixture thereof and added to a dispersion comprising the solid particles of the compound (I) or a mixture thereof in a mixture of a $C_1$-$C_5$alkanol and water at temperatures between 0°-50° C. Claim 8

According to a particularly preferred embodiment fine particles are formed from a melt in a chamber having a chamber wall in the form of a plate provided with openings into a vertical fall pipe chamber. In the upper region of the fall pipe chamber fine droplets are formed which are subsequently cooled by a surrounding cooling medium during their free fall in the fall pipe chamber. The fine particles may then be collected at the bottom of the fall pipe chamber and transferred to the mixture of the organic water-miscible solvent and water. This process step is described in full detail in WO 99/33555.

The dispersion comprising the solid particles of the compounds (I) or (II) or mixtures thereof is prepared by known methods in a mixture of an organic water-miscible solvent and water. According to a preferred embodiment a mixture of water with a $C_1$-$C_5$alkanol, e.g. methanol, is used. The amount of water present in the aqueous dispersion, to which the fine particles are added, may vary within wide limits. A range of 1.0% -50.0 weight % is suitable, particularly 2.0%-10.0 weight %.

The concentration of solid particles of the compound (I) or (II) or mixtures thereof in the mixture of the organic water-miscible solvent and water may vary within wide limits. A preferred range is from about 80.0%-95.0 weight %, particularly about 90.0%-95.0 weight %. A highly preferred range is from about 93.0%-95.0 weight %.

The dispersion is made homogeneous by conventional mixing methods, such as the ones known for preparing emulsions or suspensions. Mixing is effected thoroughly throughout the dispersion by vigorous shaking using a dispersing machine, for example a Vortex mixer, or using dispersing machines of the Polytron® type (Kinematica A G, Littau Switzerland) or dispersing machines produced by IKA (Staufen Germany), a static mixer and conventional stirring machines having a propeller, anchor or paddle blade or using a phase mixer.

In order to obtain an especially homogeneous mixture, stirring is carried out at high speed, for example using Y-beam agitators (®Ystral, ®Ultraturrax) or stirring machines produced by POLYTRON, for example POLYTRON PT 3000 or DH 30/30 or using high pressure rotor/stator mixer, for example the BUSS mixing turbine.

The time period needed for forming the dispersion may vary within wide limits and depends on a batch-wise or continuous process procedure. In a batch process a suitable time period is from 1 to 180 minutes, preferably from 10 to 60 minutes.

The invention also relates to the solid particles comprising an essentially crystalline form of a compound (I) or a compound (II) selected from the group of organic phosphites and phosphonites or mixtures thereof obtainable by the process as described above.

The solid particles formed by the process of the invention are almost 100% crystalline and virtually free of amorphous fraction.

The solid particles formed by the process of the invention are very uniform and are distinguished by excellent bulk material properties, in particular freedom from dust, good flowability and good abrasion resistance and by good shelf life stability.

The solid particles comprising in essentially crystalline form pentaerythritol tetrakis[3-(3,5-di-tert-butyl-4-hydroxyphenyl)-propionate] obtained by the process according to the invention are characterised by their heat of fusion: −45 J/g at 114.5° C. (Mettler-Toledo DSC 822, 40 µl vial, 10° C./min).

The solid particles comprising in essentially crystalline form N,N'-hexane-1,6-diyl-bis[3-(3,5-di-tert-butyl-4-hydroxyphenylpropionamide)] or mixtures thereof obtained by the process according to the invention are characterised by their heat of fusion: −90.5 J/g at 159.5° C. (Mettler-Toledo DSC822, 40 µl vial, 10° C./min).

A further embodiment of the invention relates to the process step of further processing the solid particles comprising in essentially crystalline form the compounds (I) or (II) or mixtures thereof, which is characterised in that solid particles are prepared from a melt of the compound (I), wherein $R_1$, $R_2$, $R_1'$, $R_2'$, Y, x, y and z are as defined above, or of the compound (II) or mixtures thereof and added to a dispersion comprising the solid particles of the compounds (I) or (II) or mixtures thereof in a mixture of an organic water-miscible solvent and water and the crystals obtained from the dispersion are separated and further processed to other solid particle forms. Claim 2

The crystals present in the aqueous dispersion are subsequently separated from the aqueous dispersion and may be subsequently dried, and, if desired, converted to smaller particles sizes by conventional grinding methods, such as wet grinding with a ball mill. This prevents the inclusion of air or other undesirable particles.

The separation from the aqueous dispersion includes the application of any state of the art method known for separating binary solid/liquid mixtures, e.g. filtration, centrifugation or decantation. To remove any impurity the crystalline residue may be purified by the addition of water or an aqueous solution containing the above-mentioned alcohols and subsequently dried by applying the known drying techniques, particularly by applying reduced pressure or a vacuum at elevated temperatures up to 100° C.

According to a further embodiment of the process the crystals obtained are separated from the dispersion and converted to granulates.

The term solid particle comprises in addition further processed compressed particle forms, to which pressure has been applied when forming the particles from solid aggregates or agglomerates.

The compressed particles, such as granulates, comprising the compounds (I) or (II) or mixtures thereof in essentially crystalline form obtainable by the process as defined above are also subject matter of the present invention.

Compressed particle forms are obtained by applying conventional machinery, such as internal mixers, extruders, e.g. single or twin-screw extruders or planetary roller extruders, or kneaders. If an internal mixer or extruder is employed, the process is preferably carried out continuously, whereas in a kneader the process is preferably carried out batch-wise. The dried comprimates obtained, e.g. the extrudates, may then be reduced to the desired particle sizes by applying conventional grinding or milling techniques.

The term compressed particle forms particularly relates to further processed granulates formed from powders or any other fine particles by applying conventional granulation methods, such as wet granulation or compaction.

Many methods are known for the manufacture of granules and related agglomerates. Granules may be formed from powders and other fine particles by suitable agitation in the presence of a suitable binding liquid, such as water. Granules may also be formed from powders by pressurized compaction and extrusion methods by applying pressure. Application of heat to the powder may result in the sintering and formation of agglomerates of suitable size. Drying and solidification on surfaces may also produce granular products. Solutions, suspensions or melts are applied to a heated or cooled surface, and the solids are scraped off. In spray-drying, a pumpable and dispersible feed liquid, which may be a solution, gel, paste, emulsion, slurry or melt, is sprayed into a chamber, wherein solidification occurs. The chamber is heated to evaporate the solubilising or emulsifying liquid, or cooled down to allow the solidification of a melt.

The solid particle forms, or, in the alternative, the aqueous dispersion from which the solid particle forms are prepared, or the compressed particle forms defined above optionally comprise additional additives, so-called blends, suitable for use in polymers, preferably additives customarily used for improving the chemical and physical properties of polymers containing these additives. The auxiliaries can be present in varying proportions, for example, in amounts of up to 80.0% by weight, preferably from 0.05% to 40.0% by weight, more preferably from 0.05% to 25.0% by weight, with particular preference from 0.05% to 10.0% by weight, based on the total weight of the composition.

Suitable groups of additional additives are listed up hare by way of example: antioxidants selected from the group consisting of alkylated monophenols, alkylthiomethylphenols, hydroquinones and alkylated hydroquinones, tocopherols, hydroxylated thiodiphenyl ethers, alkylidene-bis-phenols, O—, N—and S-benzyl compounds, hydroxybenzylated malonates, aromatic hydroxybenzyl compounds, triazine compounds, benzylphosphonates, acylaminophenols, esters and amides of β-(3,5-di-t-butyl-4-hydroxyphenyl)propionic acid, β-(3,5-di-t-butyl-4-hydroxy-3-methylphenyl)propionic acid, or β-(3,5-dicyclohexyl-4-hydroxyphenyl)propionic acid, ascorbic acid, aminic antioxidants, light stabilisers, phosphites, phosphines, phosponites, hydroxylamines, nitrones, thiosynergists, peroxide scavengers, polyamide stabilisers, basic co-stabilisers, nucleating agents, fillers and reinforcing agents, plasticisers, lubricants, emulsifiers, pigments, Theological additives, levelling assistants, optical brighteners, flame proofing agents, antistatic agents, blowing agents, benzofuranones and indolinones.

The incorporation into the polymer materials can be carried out, for example, by mixing in the composition and, if desired, further additives in accordance with known methods. The incorporation into the polymeric material may take place prior to or during the shaping operation or by applying the composition to the polymer, with or without subsequent evaporation of the solvent. In the case of elastomers, these can also be stabilised as lattices. The invention therefore relates in particular to compositions, wherein the dispersion defined above is incorporated into and/or chemically linked with an elastomer/polymer.

The aqueous dispersion can also be added in the form of a master batch, which contains the individual components defined above in a concentration, for example from 2.5% to 25.0% by weight, to the polymer material which is to be stabilised.

The dispersion defined above can be incorporated into polymers by the following methods:
As an emulsion or dispersion (e.g. to lattices or emulsion polymers)
As a dry mix during the mixing in of additional components or polymer mixtures
By direct addition to the processing apparatus (e.g. extruder, internal mixer, etc.)
As a solution or melt.

Therefore, the present invention also relates to the process for the preparation of the polymer composition, which comprises incorporating within the polymer material to be stabilised against oxidative, thermal or light-induced degradation the aqueous dispersion defined above.

The polymer compositions can be employed in various forms and processed to give various products, for example as or to films, fibres, tapes, moulding compounds or profiles, or as binders for coating materials, adhesives or putties. The following examples illustrate the invention:

EXAMPLES

1. Preparation of Crystalline Particles of IRGANOX 1010

1.1 Preparation of Solid Particles of IRGANOX 1010

500 g of IRGANOX 1010 is added to a 1 l double jacket reaction vessel equipped with an anchor agitator and heated to 180° C. in a nitrogen atmosphere. A 1.5 mm capillary tube is attached to the outlet. The drop size is roughly twice the size of the nozzle diameter. The drops fall on a metal plate provided with cooling coils cooled by faucet water until they solidify. The time needed for solidification is around 60 sec. The solidified particles are scraped off the metal plate.

1.2 Preparation of Crystalline Particles of IRGANOX 1010 from Methanol

An aqueous solution of 500 g methanol (93.0 weight %) is added to a 1.5 l double jacket reaction vessel equipped with anchor agitator and stirred at 220 rpm at 20° C. 500 g particles of IRGANOX 1010 as obtained by Example 1.1 are added while agitating. The mixture is kept stirring at 20° C. for 60 min. The crystalline particles are filtered off with a suction filter screen of 60 mesh and dried in an oven for 2 h at 35° C. and 2 h at 80° C. at less than 50 mbar. A particle fraction of 10% is smaller than 600μ, 50% smaller than 900μ and 90% smaller than 1400μ. The crystalline particles are characterised their heat of fusion: −45 J/g at 114.5° C. (Mettler-Toledo DSC 822, 40 μl vial, 10° C./min) and a residual moisture content of less than 10% at 150 times the gravitational acceleration.

2. Preparation of Crystalline Particles of IRGANOX 1010 from Ethanol

An aqueous solution of 800 g ethanol (90.0 weight %) is added to a 1.5 l double jacket reaction vessel equipped with anchor agitator and stirred at 220 rpm at 50° C. 50 g particles of IRGANOX 1010 as obtained by Example 1.1 are added while agitating. The mixture is stirred at 50° C. for 30 min. The crystalline particles are filtered off with a suction filter screen of 60 mesh and dried in an oven for 2 h at 35° C. and 2 h at 80° C. at less than 50 mbar. A particle fraction of 10% is smaller than 600μ, 50% smaller than 900μ and 90% smaller than 1400μ. The crystalline particles are characterised by their heat of fusion: −47 J/g at 114.1° C. (Mettler-Toledo DSC 822, 40 μl vial, 10° C./min) and a residual moisture content of less than 10% at 150 times the gravitational acceleration.

3. Preparation of Crystalline Particles of IRGANOX B 225 (1:1 Mixture IRGANOX 1010 and IRGAFOS 168) from Methanol An aqueous solution of 500 g methanol (93 weight %) is added to a 1.5 l double jacket reaction vessel equipped with an anchor agitator) and stirred at 220 rpm at 30° C. 5 g IRGANOX 1010 particles as obtained by Example 1.1 and 500 g solidified particles of IRGANOX B 225 as obtained in essentially the same manner as in Example 1.1 are added while agitating. The mixture is kept stirring at 30° C. for 360 min. The crystalline particles are filtered off with a suction filter screen of 60 mesh and dried in an oven for 2 h at 35° C. and 2 h at 80° C. at less than 50 mbar. A particle fraction of 10% is smaller than 600μ, 50% smaller than 900μ and 90% smaller than 1400μ. The crystalline particles are characterised by their heat of fusion: −20 J/g at 114.1° C. (Mettler-Toledo DSC 822, 40 μl vial, 10° C./min) and a residual moisture content of less than 10% at 150 times the gravitational acceleration.

4. Preparation of Crystalline Particles of IRGANOX 1098 from Methanol

An aqueous solution of 500 g methanol (70 weight %) is added to a 1.5 l double jacket reaction vessel (equipped with anchor agitator) and stirred at 220 rpm at 20° C. 500 g particles of IRGANOX 1098 as obtained by Example 1.1 are added while agitating. The mixture is stirred at 20° C. for 360 min. A particle fraction of 10% is smaller than 600μ, 50% smaller than 900μ and 90% smaller than 1400μ. The crystalline particles are filtered off with a suction filter screen of 60 mesh and dried in an oven for 2 h at 35° C. and 2 h at 80° C. at less than 50 mbar. The crystalline particles are characterised by their heat of fusion: −20 J/g at 114.1° C. (Mettler-Toledo DSC 822, 40 μl vial, 10° C./min) and a residual moisture content of less than 10% at 150 times the gravitational acceleration.

5. Preparation of Crystalline Particles of IRGAFOS 168 from Methanol

Add 30 g Methanol to a 100 ml beaker glass. Agitate at 500 upm. Heat it in water bath to 50° C. 30 g particles as obtained by example 1.1 are added while agitating. The mixture is agitated 90 minutes at 50° C. A particle fraction of 10% is smaller than 600μ, 50% smaller than 900μ and 90% smaller than 1400μ. The crystalline particles are filtered off with a suction filter screen of 60 mesh and dried overnight at room temperature at less than 50 mbar. The crystalline particles are characterised by their heat of fusion: −63.9 J/g at 184.5° C. (Mettler-Toledo DSC 822, 40 μl vial, 10° C./min) and a residual moisture content of less than 10% at 150 times the gravitational acceleration.

What is claimed is:

1. A process for preparing solid particles comprising an essentially crystalline form of a compound of the formula (I):

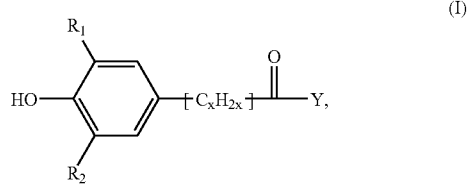

Wherein
One of $R_1$ and $R_2$ independently of one another represents hydrogen or $C_1$-$C_4$alkyl and the other one represents $C_3$-$C_4$alkyl;
x represents zero (direct bond) or a numeral from one to three; and Y represents groups of the partial formulae:

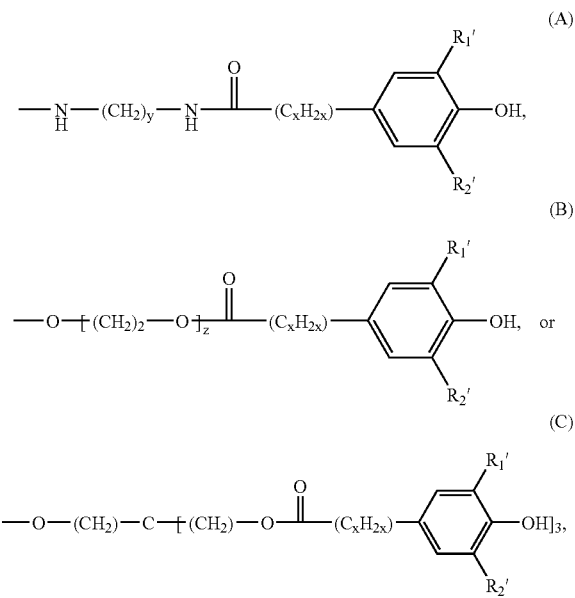

Wherein
One of $R_1'$ and $R_2'$ independently of one another represents hydrogen or $C_1$-$C_4$alkyl and the other one represents $C_3$-$C_4$alkyl;
x represents zero (direct bond) or a numeral from one to three;
y represents a numeral from two to ten; and
z represents a numeral from two to six;
characterized in that solid particles are prepared from a melt of a compound (I) by disintegration followed by full or partial solidification, the solid particles are added to a mixture of an organic water-miscible solvent and water to form a dispersion, and the crystals obtained from the dispersion are separated.

2. A process according to claim 1 which comprises further processing the crystals to other solid particle forms.

3. A process according to claim 1 for preparing solid particles comprising an essentially crystalline form of a compound (I), wherein
One of $R_1$ and $R_2$ independently of one another represents hydrogen or $C_1$-$C_4$alkyl and the other one represents $C_3$-$C_4$alkyl;
x represents zero (direct bond) or a numeral from one to three; and
Y represents groups of the partial formulae (A), (B) or (C), wherein
One of $R_1'$ and $R_2'$ independently of one another represents hydrogen or $C_1$-$C_4$alkyl and the other one represents $C_3$-$C_4$alkyl;
x represents zero (direct bond) or a numeral from one to three;
y represents a numeral from two to ten; and
z represents a numeral from two to six;
characterized in that solid particles are prepared from a melt of a compound (I) by disintegration followed by full or partial solidification, the solid particles are added to a mixture of an organic water-miscible solvent and water to form a dispersion, and the crystals obtained from the dispersion are separated.

4. A process according to claim 1, for preparing solid particles comprising an essentially crystalline form of a compound (I) or of a mixture of compounds (I), wherein
One of $R_1$ and $R_2$ independently of one another represents hydrogen or tert-butyl and the other one represents tert-butyl;
x represents two; and
Y represents groups of the partial formulae (A), (B) or (C), Wherein
One of $R_1'$ and $R_2'$ independently of one another represents hydrogen or tert-butyl and the other one represents tert-butyl;
x represents two; y represents six; and z represents two.

5. A process according to claim 1 for preparing solid particles comprising an essentially crystalline form of pentaerythritol tetrakis[3-(3,5-di-tert-butyl-4-hydroxyphenyl)-propionate] or of N,N'-hexane-1,6-diyl-bis[3-(3,5-di-tert-butyl-4-hydroxyphenylpropionamide)] or of a mixture thereof.

6. A process according to claim 1, wherein the organic solvent is a $C_1$-$C_5$alkanol.

7. A process according to claim 6, characterised in that the organic solvent is methanol.

8. A process according to claim 1, characterised in that solid particles are prepared from a melt of a compound (I) or from a melt of a mixture of compounds (I) and are added to a mixture of a $C_1$-$C_5$alkanol and water at temperatures between 0°-50° C.

9. A process according to claim 5, characterised in that the solid particles are added to a mixture of a $C_1$-$C_5$alkanol at temperatures between 20°-30° C.

* * * * *